(12) United States Patent
Hatakeyama et al.

(10) Patent No.: US 9,702,850 B2
(45) Date of Patent: Jul. 11, 2017

(54) ELECTROPHORESIS METHOD AND ELECTROPHORESIS DEVICE

(71) Applicants: SYSTEM INSTRUMENTS CO., LTD., Hachioji-shi, Tokyo (JP); NIHON UNIVERSITY, Tokyo (JP)

(72) Inventors: Yoshinori Hatakeyama, Tokyo (JP); Yoshihisa Ujima, Tokyo (JP); Nobuaki Shimura, Tokyo (JP)

(73) Assignees: SYSTEM INSTRUMENTS CO., LTD., Tokyo (JP); NIHON UNIVERSITY, Tokyo (JP)

( * ) Notice: Subject to any disclaimer, the term of this patent is extended or adjusted under 35 U.S.C. 154(b) by 146 days.

(21) Appl. No.: 14/652,583

(22) PCT Filed: Apr. 30, 2013

(86) PCT No.: PCT/JP2013/062592
§ 371 (c)(1),
(2) Date: Jun. 16, 2015

(87) PCT Pub. No.: WO2014/178107
PCT Pub. Date: Nov. 6, 2014

(65) Prior Publication Data
US 2015/0346146 A1 Dec. 3, 2015

(51) Int. Cl.
*G01N 27/453* (2006.01)
*G01N 27/447* (2006.01)
(52) U.S. Cl.
CPC . *G01N 27/44721* (2013.01); *G01N 27/44704* (2013.01); *G01N 27/44726* (2013.01); *G01N 27/44708* (2013.01)
(58) Field of Classification Search
CPC .......... G01N 27/447; G01N 27/44713; G01N 27/44721; G01N 27/453
See application file for complete search history.

(56) References Cited

U.S. PATENT DOCUMENTS 5,460,709 A * 10/1995 Sarrine ............ G01N 27/44782
204/607
7,261,800 B1 8/2007 Nakazato
(Continued)

FOREIGN PATENT DOCUMENTS

EP 0631132 A2 12/1994
JP S60-82847 A 5/1985
(Continued)

OTHER PUBLICATIONS

JPO computer-generated English language translation of JP 2001-165903 A. Downloaded Dec. 22, 2016.*
JPO computer-generated English language translation of JP 2007-114009 A. Downloaded Dec. 27, 2016.*
J PLat Pat computer-generated English language translation of JP 60-082847 A. Downloaded Dec. 27, 2016.*
(Continued)

*Primary Examiner* — Alexander Noguerola
(74) *Attorney, Agent, or Firm* — Oliff PLC

(57) ABSTRACT

To provide an electrophoresis method and an electrophoresis device which can reduce difficulty in operation while implementing sufficient staining. An electrophoresis device includes a temperature gradient tank, a dispenser, a holder storage cabinet, a photographing unit, a PCR device, a chip rack, a chip disposal box, a DC power unit, a control unit, an arm, and a liquid feeder. A holder and a cassette removably attached to the holder are put on the temperature gradient tank. The control unit controls a carrying device, the arm, the liquid feeder, the temperature gradient tank, an excitation light source and a camera in the photographing unit, and the DC power unit. The control unit prestores a program for executing the control operation in its internal memory.

8 Claims, 3 Drawing Sheets

(56) References Cited

U.S. PATENT DOCUMENTS

| | | | |
|---|---|---|---|
| 8,652,316 B1 * | 2/2014 | Chuu | G01N 27/44704 204/612 |
| 2009/0223823 A1 * | 9/2009 | Namatame | G01N 27/44726 204/469 |
| 2010/0000865 A1 | 1/2010 | Suzuki et al. | |
| 2010/0033718 A1 | 2/2010 | Tanaami | |
| 2011/0117127 A1 * | 5/2011 | Kost | G01N 27/44743 424/209.1 |

FOREIGN PATENT DOCUMENTS

| | | | | | |
|---|---|---|---|---|---|
| JP | H07-27705 | A | | 1/1995 | |
| JP | H08-35949 | A | | 2/1996 | |
| JP | 2569474 | B2 | | 1/1997 | |
| JP | 2000-338087 | A | | 12/2000 | |
| JP | 2001-165903 | A | | 6/2001 | |
| JP | 2004-286453 | A | | 10/2004 | |
| JP | 2007-114009 | A | * | 5/2007 | G01N 27/447 |
| JP | 2010-014673 | A | | 1/2010 | |
| JP | 4424938 | B2 | | 3/2010 | |
| JP | 2011-515691 | A | | 5/2011 | |

OTHER PUBLICATIONS

JPO computer-generated English language translation of JP 2004-286453 A. Downloaded Dec. 22, 2016.*

JPO computer-generated English language translation of JP 07-27705 A. Downloaded Apr. 17, 2017.*

Nov. 12, 2015 International Preliminary Report on Patentability issued in International Patent Application No. PCT/JP2013/062592.

Jun. 11, 2013 International Search Report issued in International Patent Application No. PCT/JP2013/062592.

Hatakeyama et al; "An ultimate method for detection of infected pathogenic microorganism from silkworm using HDGP;" Journal of Insect Biotechnology and Sericology; 2008; vol. 77; pp. 1-7.

Kanto Kagaku; "Rapid fluorostain kanto," brochure by Kanto Reagents; Jun. 2011; pp. 1-4.

Sep. 12, 2016 Office Action issued in Chinese Patent Application No. 201380074109.3.

Nov. 21, 2016 Office Action issued in Korean Patent Application No. 10-2015-7018839.

Dec. 8, 2016 Search Report issued in European Patent Application No. 13883485.8.

* cited by examiner

ELECTROPHORESIS METHOD AND ELECTROPHORESIS DEVICE

TECHNICAL FIELD

The present invention relates to an electrophoresis method and an electrophoresis device.

BACKGROUND ART

Various kinds of electrophoretic techniques disclosed in the following Patent Literatures have conventionally been known for example. Techniques of using electrophoresis to analyze proteins and DNA are publicly known, including an imaging technique disclosed in Patent Literature 3. Patent Literature 4 discloses analytical reagents relevant to proteins and the like.

CITATION LIST

Patent Literature

Patent Literature 1

Japanese Patent No. 2569474

Patent Literature 2

Japanese Patent Laid-Open No. 2004-286453

Patent Literature 3

Japanese Patent No. 4424938

Patent Literature 4

Japanese Patent Laid-Open No. 2010-14673

Non Patent Literature

Non Patent Document 1

Yoshinori Hatakeyama, Keiichi Hamano and Hidetoshi Iwano, (2008), An Ultimate Method for Detection of Infected Pathogenic Microoganism from Silkworm using HDGP, Journal of Insect Biotechnology and Sericology 77, 1-7

SUMMARY OF INVENTION

Technical Problem

Electrophoresis is used for analysis of deoxyribonucleic acid (DNA). The process of the analysis is as described below. First, a cassette containing gel is prepared. Then the cassette is set in a holder, and a DNA sample is dispensed to the gel. Then, the gel is soaked in a migration liquid and a DC voltage is applied thereto to perform electrophoresis. The electrophoresis disperses the DNA sample to each position on the gel. By observing the dispersed DNA sample, analysis of the DNA is implemented.

Here, when electrophoresis is performed on a DNA sample which is not stained, the sample is stained with a stain solution after electrophoresis. After the DNA sample is stained, the DNA sample is irradiated with excitation light to generate fluorescent light. As a result, DNA is observed from the outside.

In order to smoothly spread the stain solution into the gel to achieve sufficient staining, the gel is generally taken out from the cassette after electrophoresis and is soaked in the stain solution in an exposed state. However, to take out the gel from the cassette, it is necessary to carefully remove the gel from the surface of the cassette. This operation entails a very precise and delicate work, which requires mature technique. That is one of the factors that make the operation difficult.

The present invention has been made to solve the above-stated problem. Accordingly, an object of the present invention is to provide an electrophoresis method and an electrophoresis device which can reduce the difficulty in operation while implementing sufficient straining.

Solution to Problem

An electrophoresis method according to one aspect of the present invention includes:

a preparation step of providing a preparatory state wherein an end face of a gel that contains dispensed DNA is soaked in a mixed liquid containing a migration solution and a charged staining solution; and an electrophoresis step of performing electrophoresis by applying a DC voltage to the mixed liquid in the preparatory state and supplying the charged staining solution to an inside of the gel from the end face of the gel.

The electrophoresis method according to the above aspect, a temperature gradient may be provided to the gel during electrophoresis.

The electrophoresis method according to the above aspect may further includes:

an analysis step of irradiating the gel with excitation light after the electrophoresis and imaging the gel with a camera, wherein the preparation step includes: preparing a light transmissive cassette that transmits the excitation light and the imaging light of the camera; holding the gel having a planar body shape inside the cassette to expose the end face of the gel; and soaking two facing portions of the end face in the migration liquid, while infusing the staining solution into the migration liquid at least on one side of the two portions, and the electrophoresis step includes applying a voltage to the migration solution having the two portions soaked therein to pass the staining solution to a planar direction of the gel and to provide a temperature gradient to the planar direction of the gel.

The electrophoresis method according to the above aspect may be such that, after the electrophoresis step, the gel is irradiated with the excitation light through the cassette while the gel is held in the cassette, and the gel is imaged with the camera.

An electrophoresis device according to other aspect of the present invention includes:

a temperature gradient tank;

a holder including a holder body having an upper surface, a recess portion provided on the upper surface to enable a light transmissive cassette to fit therein, an electrode provided on the recess portion, and an electrode terminal coupled to the electrode;

a carrying device capable of sending out the plurality of holders onto the temperature gradient tank one by one;

dispensation means including a dispenser and an arm joined to the dispenser;

a liquid feeder that feeds a mixed liquid containing the migration solution and the staining solution;

a DC power supply;

a photographing unit including an excitation light source and a camera; and a control unit connected to the carrying device, the arm, the liquid feeding unit, the DC power supply, and the photographing unit, wherein the control unit continuously executes:

first control performed for making the carrying device to carry the holder onto the temperature gradient tank;

second control performed subsequent to the first control for making the dispenser to perform dispensing to the holder on the temperature gradient tank with the arm and making the liquid feeder to feed the mixed liquid to the recess portion;

third control performed subsequent to the second control for generating a temperature gradient in the temperature gradient tank and applying a DC voltage to the electrode terminal from the DC power supply; and fourth control performed subsequent to the third control for irradiating the cassette with light from the excitation light source and imaging the cassette with the camera.

Advantageous Effects of Invention

The electrophoresis method according to the present invention can reduce the difficulty in operation while implementing sufficient straining.

According to the electrophoresis device in the present invention, a device suitable for automatization of the electrophoresis method according to the present invention is provided.

DESCRIPTION OF EMBODIMENTS

Figure 1:
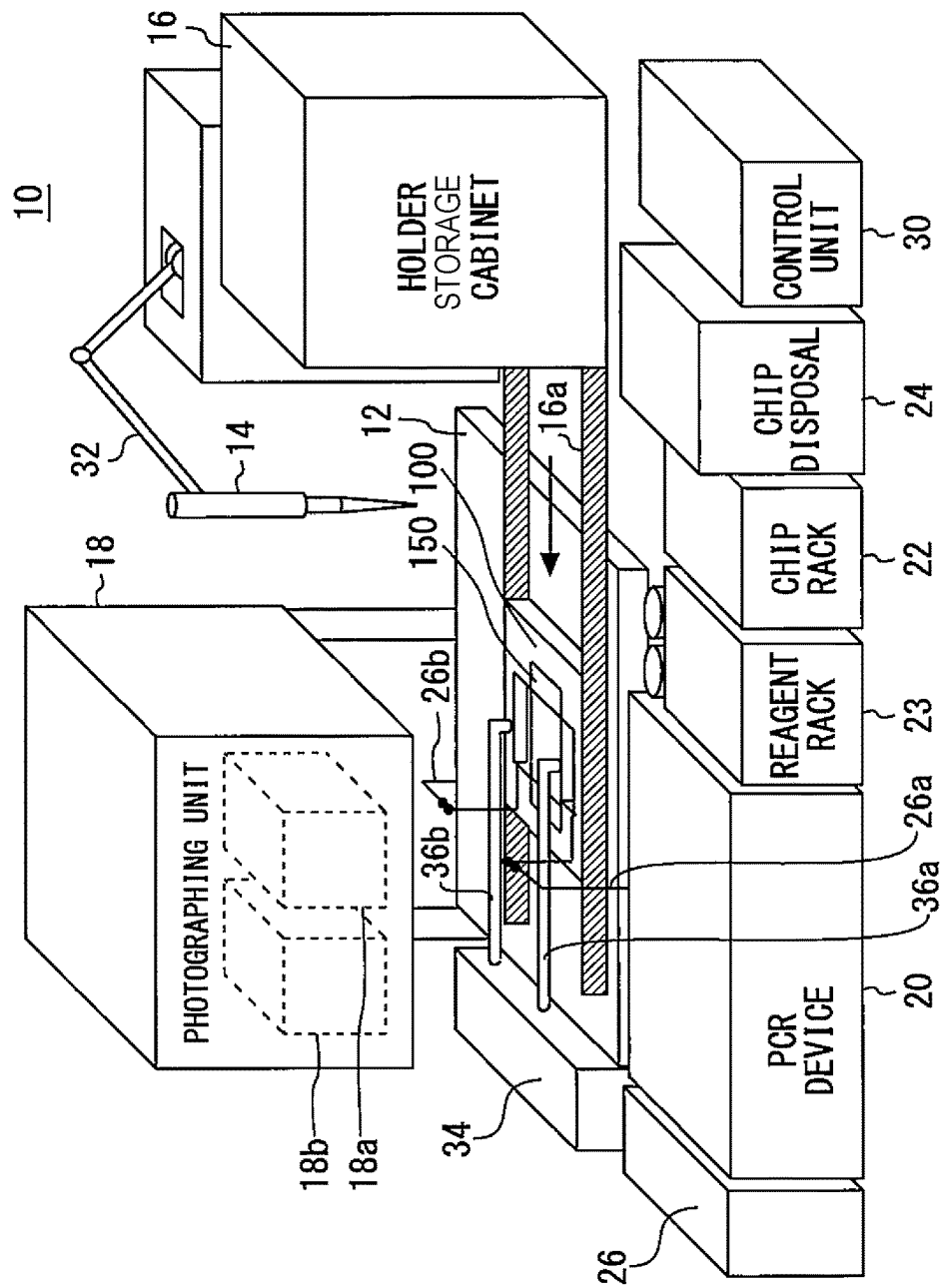
FIG. 1 is an explanatory view of the configuration of an electrophoresis device according to an embodiment of the present invention.

FIGS. 1 to 4 are explanatory views of the configuration of an electrophoresis device 10 according to an embodiment of the present invention. As illustrated in FIG. 1, the electrophoresis device 10 includes a temperature gradient tank 12, a dispenser 14, a holder storage cabinet 16, a photographing unit 18, a polymerase chain reaction (PCR) device 20, a chip rack 22, a chip disposal box 24, a DC power unit 26, a control unit 30, an arm 32, and a liquid feeder 34.

A holder 100 formed with a thermally conductive material is put on the temperature gradient tank 12. A light transmissive cassette 150 is removably attached to the holder 100. Heat can be delivered to a gel side of the cassette 150 via the holder 100.

The temperature gradient tank 12 is in contact with a bottom surface 106 of the holder 100. The temperature gradient tank 12 is provided to perform "temperature gradient electrophoresis", whereby a temperature gradient can be provided in a planar direction of the bottom surface 106. As a consequence, temperature distribution can be generated for the gel in the cassette 150.

The dispenser 14 is for dispensing a DNA sample 204 to a gel 152. The dispenser 14 is mechanically and electrically coupled with the arm 32, so that movement of the dispenser 14, filling in the dispenser 14, and discharge by the dispenser 14 can be performed through the arm 32.

The holder storage cabinet 16 houses a plurality of holders 100. The holder storage cabinet 16 includes a carrying device 16a. The carrying device 16a can send out the plurality of holders 100 housed in the holder storage cabinet 16 to a middle position of the temperature gradient tank 12 one by one.

As for the detailed configuration of the carrying device 16a, such as the structure of an actuator, various kinds of publicly known carrying devices may suitably be used. Since the carrying devices including, for example, rails that hold the side surfaces of the holder and conveyors driven by a motor may be used, the detailed description of the carrying device 16a is omitted.

The photographing unit 18 is placed above the holder 100 so as to overlook the holder 100 from the above. The photographing unit 18 includes an excitation light source 18a and a camera 18b. The excitation light source 18a is a light source for irradiating the stained DNA with excitation light through the cassette 150. The camera 18b can take an image through the cassette 150.

The photographing unit 18 may be placed at positions where the holder 100 can be overlooked as and when necessary. For example, the holder 100 may be configured to be movable on the temperature gradient tank 12 so that the holder 100 can be placed below the photographing unit 18 as and when necessary. Or the photographing unit 18 may be configured so as to be movable by means of a rail or the like and to be positioned above the holder 100 as and when necessary.

The chip rack 22 houses a plurality of components called chips, which are attached to the dispenser 14 at the time of being used. A reagent rack 23 is to set a reagent for use in performing electrophoresis. The reagent is what is called a loading buffer. The DNA sample 204 and this reagent are mixed, and the mixture is dispensed to the gel 152. This makes it possible to prevent diffusion of the DNA sample 204 and to thereby stabilize the DNA sample 204 when the DNA sample 204 is dispensed to the gel 152. The chip disposal box 24 is a storage cabinet which houses used chips.

The DC power unit 26 is for outputting a DC voltage for electrophoresis. The DC power unit 26 includes a pair of output terminals 26a and 26b. When the holder 100 is sent out onto the temperature gradient tank 12, the output terminals 26a and 26b are precisely connected to the electrode terminals 121 and 123 of the holder 100.

The liquid feeder 34 includes, in its interior, a migration solution tank, a staining solution tank, a mixer to mix the migration solution and the staining solution, and a pump. The liquid feeder 34 can feed the migration solution and the staining solution to prescribed positions of the holder 100 via pipelines 36a and 36b.

The control unit 30 can control the carrying device 16a of the holder storage cabinet 16. The control unit 30 can control the carrying device 16a to send out the holder 100 one by one.

The control unit 30 is connected to the arm 32. The control unit 30 can control the dispenser 14 via the arm 32 to execute sucking operation, stirring operation, placing operation, and discharge operation. The sucking operation is the operation wherein the dispenser 14 attaches a chip in the chip rack 22 to itself and sucks the DNA sample 204 from the PCR device 20. The stirring operation is the operation wherein the dispenser 14 repeats suction and discharge to mix the DNA sample 204 sucked from the PCR device 20 with the reagent in the reagent rack 23. The placing operation is the operation to move the dispenser 14 to a prescribed position of the reagent rack 23 and/or a prescribed position in the holder 100 on the temperature gradient tank 12 for stirring operation. The discharge operation is the operation wherein the dispenser 14 discharges the DNA sample 204, which was mixed with the reagent in the chip that is attached to the dispenser 14, at a prescribed position in the holder 100.

The control unit 30 is connected with the liquid feeder 34. By controlling the liquid feeder 34, the migration solution and the mixed liquid are fed to prescribed positions of the holder 100 via the pipelines 36a and 36b at predetermined timing.

The control unit 30 is connected to the temperature gradient tank 12, the excitation light source 18a and the camera 18b in the photographing unit 18, and to the DC power unit 26. As a consequence, the control unit 30 can perform temperature gradient electrophoresis for a predetermined period of time by giving a predetermined temperature gradient to the holder 100 while applying a given direct current voltage from the DC power unit 26. After the electrophoresis is performed for the predetermined period of time, the control unit 30 irradiates the gel 152 with excitation light through the cassette 150, and takes an image with the camera 18b.

Figure 2:
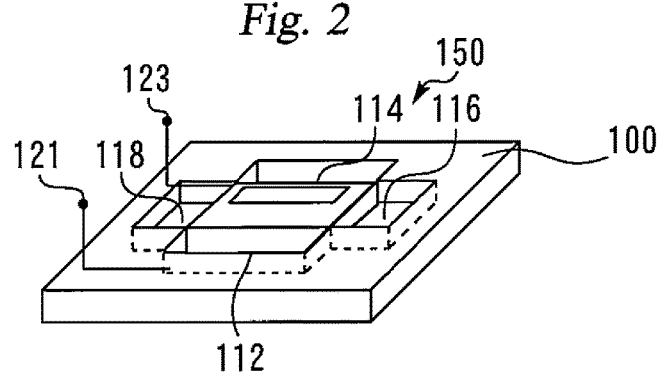
FIG. 2 is an explanatory view of the configuration of an electrophoresis device according to an embodiment of the present invention.
Figure 3:
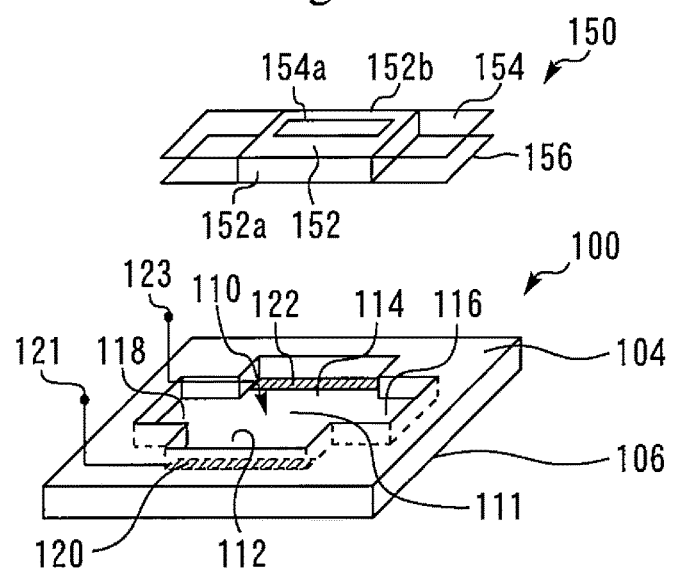
FIG. 3 is an explanatory view of the configuration of an electrophoresis device according to an embodiment of the present invention.
Figure 4:
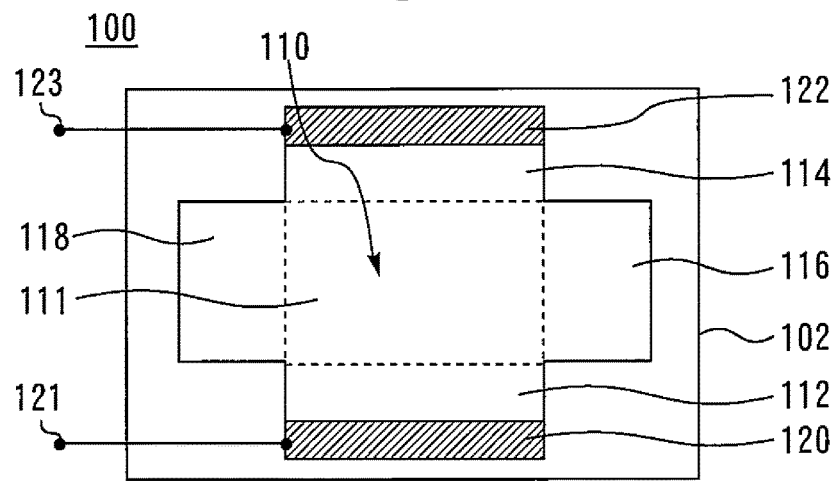
FIG. 4 is an explanatory view of the configuration of an electrophoresis device according to an embodiment of the present invention.

FIG. 2 is a perspective view for describing the configuration of the holder 100 and the cassette 150 according to the embodiment of the present invention, and FIG. 3 is an exploded perspective view of FIG. 2. FIG. 4 is a plan view for describing the configuration of the holder 100 and the cassette 150 according to the embodiment of the present invention.

The cassette 150 is made up of a pair of transparent plates 154 and 156. The transparent plates 154 and 156, which are formed of glass or light transmissive resin, can deliver heat to the gel 152 held therebetween. A penetrating groove 154a is provided on the transparent plate 154 positioned on the upper side. Part of the gel 152 is exposed from the penetrating groove 154a.

The holder 100 includes a holder body 102 including an upper surface 104 and a bottom surface 106. The holder body 102 is formed of glass or light transmissive resin and has thermal conductivity to conduct the heat received on the bottom surface 106 to the cassette 150. A recess portion 110 is provided on the upper surface 104 of the holder body 102. The recess portion 110 is a hollow having a cross like outline as a whole. The depth of the recess portion 110 is made equal to or more than the thickness of the entire cassette 150 with the gel 152 held therein.

The recess portion 110 has a central portion 111 positioned in the middle of the cross like outline. The recess portion 110 is provided with liquid supply portions 112 and 114 and frame portions 116 and 118 provided around the central portion 111 at positions perpendicular to each other in a plane view. The frame portions 116 and 118 have the same outline as the cassette 150, so that the cassette 150 can be fitted therein. The liquid supply portions 112 and 114 are members protruding outward from the frame portions 116 and 118. The liquid supply portions 112 and 114 form a space to contain liquid when the cassette 150 is fitted in the recess portion 110. Since the end portions 152a and 152b of the gel 152 are exposed from the liquid supply portions 112 and 114, liquid can be injected into the liquid supply portions 112 and 114 so that the end portions 152a and 152b can be soaked in the liquid.

The recess portion 110 is provided with electrodes 120 and 122 electrically insulated from each other. The electrodes 120 and 122 are exposed to the liquid supply portions 112 and 114 when the cassette 150 is set. The electrodes 120 and 122 are coupled with the electrode terminals 121 and 123, and the electrode terminals 121 and 123 are coupled to the DC power unit 26.

Figure 5:
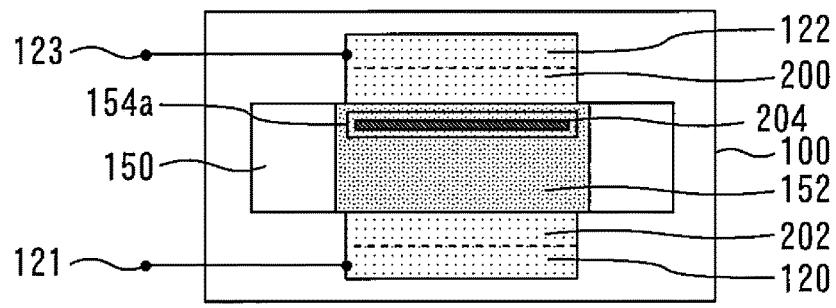
FIG. 5 is an explanatory view of the electrophoresis method and a method for using an electrophoresis device according to the embodiment of the present invention.
Figure 6:
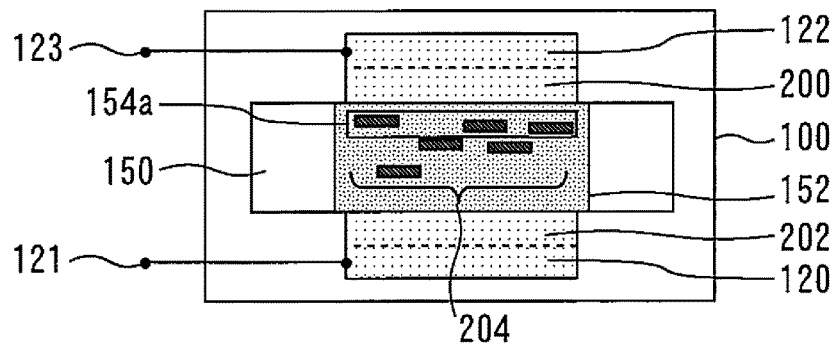
FIG. 6 is an explanatory view of the electrophoresis method and a method for using an electrophoresis device according to the embodiment of the present invention.

FIGS. 5 and 6 are explanatory views of the electrophoresis method and a method for using an electrophoresis device according to the embodiment of the present invention. FIGS. 5 and 6 illustrate the cassette 150 before and after electrophoresis as viewed from the above, respectively. The cassette 150 with the gel 152 held therein is attached to the holder 100.

In performing electrophoresis, the migration solution 200 is injected to the liquid supply portion 112, and the mixed liquid 202 is injected to the liquid supply portion 114. The mixed liquid 202 is formed by mixing the migration solution 200 with the staining solution.

Next, the electrode terminals 121 and 123 are coupled with the DC power unit 26 to provide a positive potential to the electrode 120 and a negative potential to the electrode 122. Accordingly, a DC voltage is applied to between the electrodes 120 and 122, and an electric current passes to the migration solution 200 and the mixed liquid 202. As a result, electrophoresis of the DNA sample 204 is performed.

The staining solution and the migration solution are mixed before electrophoresis is started. A charged staining solution is used as the staining solution. By performing the electrophoresis in such a state, the staining solution infiltrates into the gel 152 together with the migration solution based on the principle of electrophoresis. As a result, electrophoresis and staining of the DNA sample 204 can collectively be performed.

Since the DNA is negatively charged, positively charged staining solution may preferably be used. Using the positively charged staining solution causes the DNA and the staining solution to move in opposite directions during electrophoresis. As a result, the DNA and the staining solution are combined so that reliable staining of the DNA is conducted.

Specifically, any one of SYBR (registered trademark) DNA staining dye series including SYBR Green I, SYBR Green II, SYBR Gold, and SYBR Safe, may be used. Any one of YO (Oxazole Yellow), TO (Thiazole Orange), or PG (Pico (registered trademark) Green) may also be used.

In this embodiment in particular, the temperature gradient tank 12 is controlled to generate a temperature gradient inside the surface of the gel 152. Accordingly, temperature gradient electrophoresis is performed. By performing the temperature gradient electrophoresis for a predetermined period of time, the DNA sample 204 moves as illustrated in FIG. 6. By analyzing this movement, DNA analysis can be conducted.

Figure 7:
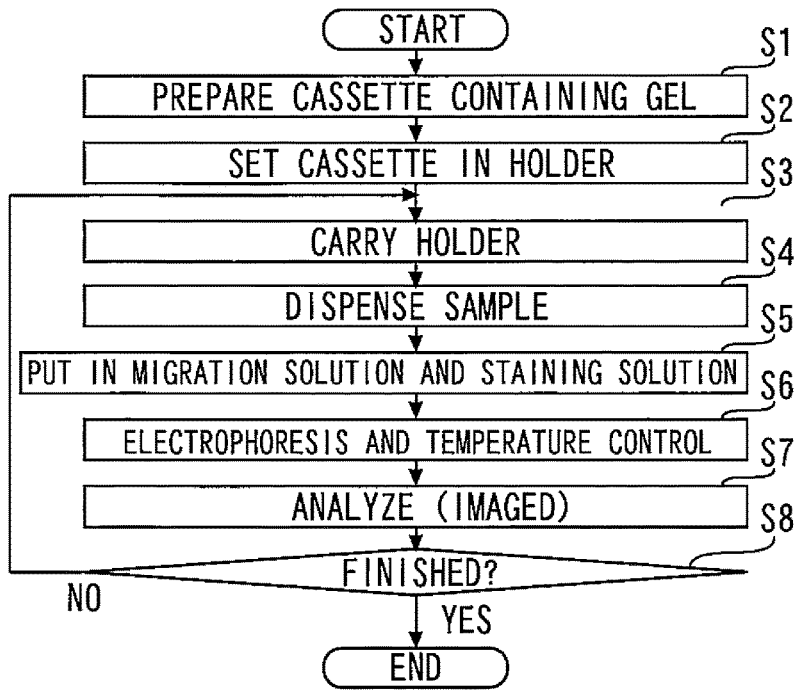
FIG. 7 is an explanatory view of the electrophoresis method and an operation of an electrophoresis device according to the embodiment of the present invention.

FIG. 7 is a flow chart for describing the electrophoresis method and the operation of the electrophoresis device according to the embodiment of the present invention.

The electrophoresis device 10 according to the present embodiment is suitable for the electrophoresis method involving mixing of the migration solution and the staining solution. More specifically, the control unit 30 can control the carrying device 16a, the arm 32, the liquid feeder 34, the temperature gradient tank 12, the excitation light source 18a and the camera 18b in the photographing unit 18, and the DC power unit 26. Hereinbelow, control operation performed by the control unit 30 will also be described. The control unit 30 prestores a program for executing the following control operation in its internal memory.

(Step S1) First, the cassette 150 containing the gel 152 is prepared. In this step, the cassette 150 has light transmission that transmits excitation light and imaging light of the camera. The gel 152 has a planar body shape. The cassette 150 has the gel 152 held therein so as to expose the end portions 152a and 152b.

(Step S2) Next, the cassette 150 is set in the holder 100. The plurality of holders 100 are prepared, and are housed at prescribed positions inside the holder storage cabinet 16. This enables the carrying device 16a to carry the plurality of holders 100 one by one, so that multiple analyzing operations can be performed continuously and automatically.

(Step S3) Next, the holder 100 is carried to the middle position of the temperature gradient tank 12. In the electrophoresis device 10 according to the present embodiment, this carrying operation is automatically performed by the carrying device 16a.

(Step S4) Next, the DNA sample 204 is dispensed. As described in the foregoing, the control unit 30 controls the dispenser 14 via the arm 32 to execute sucking operation, stirring operation, placing operation, and discharge operation. In the discharge operation, the DNA sample 204 is dispensed from the penetrating groove 154a, so that the DNA sample 204 is dispensed to the end face of the gel 152 on the side of the liquid supply portion 114, i.e., on the end portion 152b side. The DNA sample 204 is uniformly dispensed in parallel with the end portion 152b in an extending direction of the end portion 152b.

In the electrophoresis device 10, dispensation of the DNA sample 204 in step S4 is implemented when the control unit 30 sends a control signal to the arm 32 as described in the foregoing. As a consequence, automatic dispensation of the DNA sample 204 can be achieved.

(Step S5) Next, the migration solution and the staining solution are put in the holder 100. More specifically, the mixed liquid 202 is put into the liquid supply portion 112, and the migration solution 200 is put into the liquid supply portion 114. Accordingly, two facing portions in the end face of the gel 152, i.e., the end portions 152a and 152b are soaked in the migration solution. Then, the migration solution at least on one side of the end portion 152a and the end portion 152b is infused with the staining solution. According to this embodiment, only the migration solution 200 is put into the liquid supply portion 114, and the mixed liquid 202 formed by mixing the migration solution and the staining solution is put into the liquid supply portion 112. This provides a preparatory state wherein the end face of the gel containing a dispensed DNA is soaked in the mixed liquid 202.

In the electrophoresis device 10, the control unit 30 controls the liquid feeder 34, so that a specified amount of the migration solution 200 and the mixed liquid 202 is each fed to the liquid supply portions 112 and 114 by the pump inside the liquid feeder 34.

Step S4 and step S5 may reversely be performed.

(Step S6) Next, a DC voltage is applied to the migration solution to perform electrophoresis, while the temperature gradient tank 12 is controlled to provide a temperature gradient to the gel during electrophoresis. By applying a voltage to the migration solution in which the end portions 152a and 152b are soaked, the staining solution is passed in the planar direction of the gel, and a temperature gradient is provided in the planar direction of the gel.

In the electrophoresis device 10, the control unit 30 controls the temperature gradient tank 12 and the DC power unit 26, so that automatic electrophoresis is performed under predetermined conditions (predetermined temperature inclination, predetermined applied voltage, and predetermined time).

(Step S7) After electrophoresis is performed, the gel 152 is irradiated with excitation light and is imaged with the camera 18b. In this step, after electrophoresis is performed, the gel 152 is irradiated with excitation light through the cassette 150, and is imaged with the camera 18b. In order to avoid a reflection problem, the direction of the excitation light source 18a may be adjusted to irradiate the gel 152 with inclined excitation light. In the electrophoresis device 10, the control unit 30 controls the excitation light source 18a and the camera 18b, so that the operation of step S7 is automatically implemented.

(Step S8) When the process of step S7 is completed, it is determined whether or not the current DNA analysis operation is finished. If one analysis operation is scheduled this time, the current routine is ended. If multiple analysis operations are scheduled, subsequent analysis operations are similarly performed by using other holders 100 until the scheduled number of analysis operations are finished.

In the electrophoresis device 10, the holder 100 of this time is removed manually or automatically by another machine, and then the carrying device 16a sends out a new holder 100. As a result, replacement of the holder 100 is performed, and the control operation of steps S3 to S8 is repeated.

Then, once the number of analysis operations reaches the scheduled number of operations, the current routine is ended.

According to the electrophoresis method in the embodiment described above, electrophoresis and staining of the DNA are collectively performed, while the charged staining solution is injected into the gel with the driving force of electrophoresis, so that sufficient staining can be achieved. Therefore, the difficulty in operation can be reduced, while sufficient staining is implemented.

Moreover, the present embodiment provides the electrophoresis device 10 which automates the electrophoresis method according to the present embodiment.

According to the electrophoresis method in the present embodiment described above, the gel has a thin planar body, so that an accurate temperature gradient can easily be provided. Therefore, the method is suitable for temperature gradient electrophoresis.

It is difficult to achieve sufficient staining in a short period of time by simply soaking a thin gel held inside the cassette. However, according to the present embodiment, the staining solution which obtained driving force by the electrophoresis infiltrates into the gel. Accordingly, even in the case of a thin planar gel, the staining solution can sufficiently impregnate the gel in its planar direction.

According to the present embodiment, sufficient staining can be implemented without removing the gel from the cassette. Accordingly, the difficulty in operation of removing the cassette is eliminated. Furthermore, the gel can be irradiated with excitation light through the cassette and be imaged with a camera. In addition, electrophoresis and staining can be performed in one process, so that the process can be simplified and the speed thereof can be increased.

Moreover, according to the present embodiment, staining with the staining solution is performed in analysis operation, so that analysis accuracy and reliability of analysis results are high. In the case of using a DNA sample stained (labeled) before electrophoresis, analysis accuracy and the like are questionable. As compared with the above case, the present embodiment has high superiority.

The electrophoresis method according to the present embodiment characterized as described before is also adequate for what is called a hyper detection of infectious disease based on genome profiling (HDGP) method as disclosed in Non Patent Document 1 described above.

REFERENCE SIGNS LIST 10 electrophoresis device
12 temperature gradient tank
14 dispenser
16 holder storage cabinet
16a carrying device
18 photographing unit
18a excitation light source
18b camera
20 polymerase chain reaction (PCR) device
22 chip rack
reagent rack
24 chip disposal box
26 DC power unit
26a, 26b output terminal
30 control unit
32 arm
34 liquid feeder
36a, 36b pipeline
100 holder
102 holder body
104 upper surface
106 bottom surface
110 recess portion
111 central portion
112, 114 liquid supply portion
116 frame portions
120, 122 electrodes
121, 123 electrode terminal
150 cassette
152 gel
152a, 152b end portion
154 transparent plate
154a penetrating groove
200 migration solution
202 mixed liquid
204 DNA sample

The invention claimed is:

1. An electrophoresis device, comprising:
a temperature gradient device generating a temperature gradient;
a holder including a holder body having an upper surface, a recess portion provided on the upper surface to enable a light transmissive cassette to fit therein, at least one electrode provided on the recess portion, and an electrode terminal coupled to the at least one electrode;
a carrying device capable of sending out a plurality of holders onto the temperature gradient device one by one;
dispensation means including a dispenser;
a liquid feeder that feeds a mixed liquid containing a migration solution and a staining solution;
a DC power supply;
a photographing unit including an excitation light source and a camera; and
a control unit connected to the carrying device, the dispensation means, the liquid feeder, the DC power supply, and the photographing unit, wherein
the control unit is configured to continuously executes the following control operations:
first control performed for making the carrying device to carry the holder onto the temperature gradient device;
second control performed subsequent to the first control for making the dispenser to perform dispensing to the holder on the temperature gradient device with an arm of the electrophoresis device and making the liquid feeder to feed the mixed liquid to the recess portion;
third control performed subsequent to the second control for generating a temperature gradient in the temperature gradient device and applying a DC voltage to the electrode terminal from the DC power supply; and
fourth control performed subsequent to the third control for irradiating the cassette with light from the excitation light source and imaging the cassette with the camera.

2. The electrophoresis device according to claim 1, further comprising:
a chip rack having a plurality of chips;
a polymerase chain reaction (PCR) device having a DNA sample; and
a reagent rack having a reagent;
wherein:
the second control includes performing a sucking operation, a stirring operation, a placing operation, and a discharge operation,
the sucking operation is an operation in which the dispenser attaches a chip in the chip rack to itself and sucks the DNA sample from the PCR device,
the stirring operation is an operation in which the dispenser repeats suction and discharge to mix the DNA sample sucked from the PCR device with the reagent in the reagent rack,
the placing operation is an operation to move the dispenser to a first prescribed position of the reagent rack and to a second prescribed position in the holder on the temperature gradient tank for stirring operation, and
the discharge operation is an operation wherein the dispenser discharges the DNA sample, which was mixed with the reagent in the chip that is attached to the dispenser, at the second prescribed position.

3. The electrophoresis device according to claim 1, wherein:
the cassette includes a pair of plates, a gel having a planar shape and having a first surface and a second surface opposing to the first surface, wherein the gel is held between the pair of plates so that one of the plates contacts the first surface and the other of the plates contacts the second surface, the recess portion has a central portion where the gel held with the cassette is to be provided, a first liquid supply portion and a second liquid supply portion being provided around the central portion, the first liquid supply portion sandwiching the central portion with the second liquid portion in a plane view, a first end portion of the gel is exposed from the first liquid supply portion, a second end portion of the gel is exposed from the second liquid supply portion, the at least one electrode includes a first electrode provided in the first liquid supply portion and a second electrode provided in the second liquid supply portion, the liquid feeder is configured to selectively perform a first feeding and a second feeding, the first feeding is to feed only the migration solution among the migration solution and the staining solution, the second feeding is to feed mixed liquid of the migration solution and the staining solution, the second control includes a first feeding control and a second feeding control, the first feeding control causes the liquid feeder to perform the first feeding into the first liquid supply portion so that the first end portion and the first electrode are soaked in the migration solution, the second feeding control causes the liquid feeder to perform the second feeding into the second liquid supply portion so that the second end portion and the second electrode are soaked in the mixed liquid.

4. The electrophoresis device according to claim 1, wherein the holder body includes a bottom surface, and the temperature gradient device is configured to perform the temperature gradient in a planar direction of the bottom surface on the temperature gradient device.

5. The electrophoresis device according to claim 1, wherein the upper surface of the recess portion is configured to allow the light transmissive cassette to fit in the recess portion and also to include a pair of plates, a gel having a planar shape and having a first surface and a second surface opposing to the first surface is held between the pair of plates so that one of the plates contacts the first surface and the other of the plates contacts the second surface, one of the plates includes a penetrating groove for exposing a part of the first surface of the gel, and the second control, when executed by the control unit, causes the dispenser to dispense a sample to the part of the first surface of the gel exposed from the penetrating groove.

6. The electrophoresis device according to claim 1, wherein the control unit is programmed to execute a detection of infectious disease based on genome profiling based on an image obtained by the fourth control.

7. The electrophoresis device according to claim 1, wherein the staining solution is positively charged.

8. An electrophoresis device, comprising:

a stage;

a holder including a holder body having an upper surface, a recess portion provided on the upper surface to enable a light transmissive cassette to fit therein, an electrode provided on the recess portion, and an electrode terminal coupled to the electrode;

a carrying device capable of sending out a plurality of holders onto the stage one by one;

dispensation means including a dispenser and an arm joined to the dispenser;

a liquid feeder that feeds a mixed liquid containing a migration solution and a staining solution;

a DC power supply;

a photographing unit including an excitation light source and a camera; and a control unit connected to the carrying device, the arm, the liquid feeder, the DC power supply, and the photographing unit, wherein the control unit is configured to continuously execute the following operations:

first control performed for making the carrying device to carry the holder onto the stage;

second control performed subsequent to the first control for making the dispenser to perform dispensing to the holder on the stage with the arm and making the liquid feeder to feed the mixed liquid to the recess portion;

third control performed subsequent to the second control for applying a DC voltage to the electrode terminal from the DC power supply; and fourth control performed subsequent to the third control for irradiating the cassette with light from the excitation light source and imaging the cassette with the camera.

* * * * *